(12) United States Patent
Yang

(10) Patent No.: US 12,285,172 B2
(45) Date of Patent: Apr. 29, 2025

(54) DISASSEMBLABLE ANASTOMOSIS CLAMP

(71) Applicant: HeronScope Medical Technology Development (Shanghai) Co., Ltd, Shanghai (CN)

(72) Inventor: Guang Yang, Shanghai (CN)

(73) Assignee: HeronScope Medical Technology Development (Shanghai) Co., Ltd, Shanghai (CN)

( * ) Notice: Subject to any disclaimer, the term of this patent is extended or adjusted under 35 U.S.C. 154(b) by 526 days.

(21) Appl. No.: 17/761,542

(22) PCT Filed: Feb. 21, 2020

(86) PCT No.: PCT/CN2020/076274
§ 371 (c)(1),
(2) Date: Mar. 17, 2022

(87) PCT Pub. No.: WO2021/051740
PCT Pub. Date: Mar. 25, 2021

(65) Prior Publication Data
US 2022/0338875 A1    Oct. 27, 2022

(30) Foreign Application Priority Data

Sep. 18, 2019  (CN) .......................... 201910880471.9
Sep. 18, 2019  (CN) .......................... 201910880473.8
(Continued)

(51) Int. Cl.
*A61B 17/11*    (2006.01)
(52) U.S. Cl.
CPC .................................... *A61B 17/11* (2013.01)

(58) Field of Classification Search
CPC ............ A61B 17/11; A61B 2017/1103; A61B 17/122; A61B 17/1114
See application file for complete search history.

(56) References Cited

U.S. PATENT DOCUMENTS 4,474,181 A * 10/1984 Schenck ................ A61B 17/11
606/155
2002/0058955 A1 * 5/2002 Blatter ............... A61B 17/0643
606/139
(Continued)

FOREIGN PATENT DOCUMENTS

CN    201263700 Y    7/2009
CN    201564544 U    9/2010
(Continued)

OTHER PUBLICATIONS

International Search Report of PCT/CN2020/076274.
Written Opinion of PCT/CN2020/076274.

*Primary Examiner* — Robert A Lynch
*Assistant Examiner* — Christina C Lauer

(57) ABSTRACT

A disassemblable anastomosis clamp, at least comprising a clamp frame and a first clasping part and a second clasping part connected to the clamp frame. The first clasping part and/or the second clasping part is detachably connected to the clamp frame. At least one clasping part is designed to be detachable from the clamp frame, and thus when removing the anastomosis clamp, the detachable clasping part can be separated from the clamp frame first and then moved away, allowing the anastomosis clamp to be removed safely and conveniently.

3 Claims, 23 Drawing Sheets

(30) Foreign Application Priority Data

Sep. 18, 2019 (CN) .......................... 201910880474.2
Sep. 18, 2019 (CN) .......................... 201910880854.6

(56) References Cited

U.S. PATENT DOCUMENTS

2011/0208210 A1    8/2011  Baur et al.
2017/0231630 A1*  8/2017  Schurr .................. A61L 31/022
                                                  606/151

FOREIGN PATENT DOCUMENTS

| CN | 204542351 U | 8/2015 |
| CN | 109044473 A | 12/2018 |
| CN | 110477989 A | 11/2019 |
| CN | 110559038 A | 12/2019 |
| CN | 110575218 A | 12/2019 |

* cited by examiner

DISASSEMBLABLE ANASTOMOSIS CLAMP

CROSS REFERENCE TO RELATED APPLICATIONS

This Application is a national stage application of PCT/CN2020/076274. This application claims priorities to PCT Application No. PCT/CN2020/076274, filed on Feb. 21, 2020, Chinese Patent Applications No. 201910880854.6, 201910880473.8, 201910880474.2 and 201910880471.9, filed to CNIPA on Sep. 18, 2019 and entitled "Disassemblable Anastomosis clamp", "Clamping Cap and Anastomosis Device With Same", "Beveled Clamping Cap and Anastomosis Device With Same" and "Duckbilled Clamping Cap and Anastomosis Device with Same", the entire contents of which are incorporated herein by reference.

FIELD

The disclosure relates to the field of anastomosis clamps, in particular to a disassemblable anastomosis clamp.

BACKGROUND

An anastomosis clamp can be used for fixation or marking, for example, for fixing an esophageal stent or an intestinal stent or marking the position of tissues, and can also be used for anastomoses of tissues in the gastrointestinal tract (also used in anal fistulas) to achieve wound closure or hemostasis, for example, wound closure and hemostasis in gastroscopy or laparoscopy or open surgery. When the anastomosis clamp is used for fixing stents, most of the stents need to be removed by a second operation. When the anastomosis clamp is used for anastomoses of tissues, the anastomosis clamp also needs to be detached and removed after the operation since people may fear for its retention in the body. The existing anastomosis clamps are all of single-piece design, and thus, are difficult to detach and prone to secondary trauma. In view of this problem, Chinese Patent No. 201820924609.1 (CN209059324U) discloses a disassemblable anastomosis clamp, however, the disassemblable anastomosis clamp has problems that the binding type structure is complex, the parts are trivial, and the binding type causes the disassemblable anastomosis clamp to easily become loose, resulting in unstable excitation force, insufficient clasping force and complicated detachment process. In addition, the existing anastomosis clamps have limited closing force, resulting in incomplete closure.

SUMMARY

The purpose of the disclosure is to provide a disassemblable anastomosis clamp, in order to solve the problem of difficulty in detachment, complex structure and/or small closing force in the existing anastomosis clamps.

The solution adopted by the disclosure is as follows: a disassemblable anastomosis clamp at least includes a clamp frame and a first clasping part and a second clasping part connected to the clamp frame. The first clasping part and/or second clasping part is detachably connected to the clamp frame.

Further, the clamp frame is a closed outer frame.

Further, the first clasping part and/or the second clasping part is a toothed piece connected to the inside of the closed outer frame, and the toothed piece is provided with at least one tooth.

Further, the closed outer frame includes an upper arm, a left side arm, a lower arm and a right side arm, and the upper arm, the left side arm, the lower arm and the right side arm are sequentially connected to form the closed outer frame.

Further, the first clasping part and the second clasping part are respectively connected to the upper arm and the lower arm. The first clasping part is detachably connected to the upper arm and/or the second clasping part is detachably connected to the lower arm.

Further, the first clasping part and/or the second clasping part includes at least one fixing groove, and the clamp frame at least includes a protrusion inserted into and matched with the fixing groove.

Further, the fixing groove includes a first fixing groove and a second fixing groove, the first fixing groove and the second fixing groove are disposed on opposite side surfaces of the clasping part, and the clamp frame includes a first protrusion inserted into and matched with the first fixing groove and a second protrusion inserted into and matched with and the second fixing groove.

Further, the fixing groove further includes a third fixing groove, the clamp frame further includes a third protrusion inserted into and matched with the third fixing groove, and the third fixing groove and the first fixing groove are respectively located on opposite side surfaces of the clasping part or the third fixing groove and the second fixing groove are respectively located on opposite side surfaces of the clasping part.

Further, the second fixing groove and the third fixing groove are respectively located on two sides of the first fixing groove. The second fixing groove and the third fixing groove are located on a same side surface of the clasping part.

Further, the first fixing groove is provided with a protruding portion or a fixing hole, and the first protrusion is provided with a fixing hole matched with the protruding portion or a protruding portion; and/or the second fixing groove is provided with a protruding portion or a fixing hole, and the second protrusion is provided with a fixing hole matched with the protruding portion or a protruding portion; and/or the third fixing groove is provided with a protruding portion or a fixing hole, and the third protrusion is provided with a fixing hole matched with the protruding portion or a protruding portion.

Further, the protruding portion is a hemispherical protrusion.

Further, the first clasping part and/or the second clasping part is detachably connected to the clamp frame by means of tying.

Further, the first clasping part and/or the second clasping part includes a clasping body and a tying body fixedly connected to the clasping body, and the tying body includes at least one tying hole. The clamp frame includes a tying body cooperation portion cooperating with the tying body, and the tying body cooperation portion includes at least one hole cooperating with the tying hole in the tying body.

Further, the tying body includes a first tying body and a second tying body that are symmetrically fixed to two sides of the clasping body, and the first tying body and the second tying body each include at least one tying hole. Correspondingly, the tying body cooperation portion includes a first cooperation portion cooperating with the first tying body and a second cooperation portion cooperating with the second tying body, and the first cooperation portion and the second cooperation portion include holes cooperating with the tying holes in the first tying body and the second tying body.

Further, the anastomosis clamp further includes a third tying body fixedly connected to the first tying body, the second tying body and the clasping body and located therebelow. The third tying body includes at least one tying hole. Correspondingly, the tying body cooperation portion includes a third cooperation portion cooperating with the third tying body, and the third cooperation portion includes at least one hole cooperating with the tying hole in the third tying body.

Further, the middle of the third tying body is provided with a slotted hole, and the third cooperation portion also includes a slotted hole cooperating with the slotted hole.

Further, the first clasping part and/or the second clasping part includes a clasping body, the clasping body includes a first radial beam and a second radial beam, and a back surface of the first radial beam is concave relative to the second radial beam to form a first recessed portion. Correspondingly, the clamp frame includes a third radial beam matched with the first radial beam and a fourth radial beam matched with the second radial beam, and a back surface of the fourth radial beam is concave relative to the third radial beam to form a second recessed portion. The third radial beam is inserted into the first recessed portion, and the second radial beam is inserted into the second recessed portion. The second radial beam and/or the first radial beam includes at least one tying hole, and the fourth radial beam and/or the third radial beam includes at least one hole cooperating with the tying hole.

Further, a front surface of the fourth radial beam is convex relative to the third radial beam, and a front surface of the first radial beam is convex relative to the second radial beam.

Further, the second radial beam further includes a slotted hole located in the middle, and correspondingly, the fourth radial beam includes a slotted hole cooperating with a slotted hole in the second radial beam.

Further, the anastomosis clamp further includes a fifth radial beam. The fifth radial beam and the first radial beam are symmetrically disposed on two sides of the second radial beam. Correspondingly, the clamp frame includes a sixth radial beam matched with the fifth radial beam.

Further, a back surface of the fifth radial beam is concave relative to the second radial beam to form a third recessed portion. The sixth radial beam is inserted into the third recessed portion.

Further, the left side arm and the right side arm are of an inward arc structure or an outward arc structure.

Further, the first clasping part and/or the second clasping part includes a clasping body, and the clasping body includes a first radial beam, a second radial beam and a first extending portion located between the first radial beam and the second radial beam and extending at a same position in a same radial direction as the first radial beam and the second radial beam. A first connecting portion is also provided between the first radial beam and the second radial beam, and the first connecting portion is connected with a second extending portion extending in the same direction as the first extending portion. The first extending portion and the second extending portion are spaced apart in the radial direction, and the first radial beam and the second radial beam are convex relative to the first extending portion and the second extending portion to respectively form a first recessed portion and a second recessed portion on back surfaces of the first radial beam and the second radial beam. Correspondingly, the clamp frame includes a third radial beam matched with the first radial beam and a fourth radial beam matched with the second radial beam, and a third extending portion located between the third radial beam and the fourth radial beam and extending at a same position in a same radial direction as the third radial beam and the fourth radial beam. A second connecting portion is also provided between the third radial beam and the fourth radial beam, and the second connecting portion is connected with a fourth extending portion extending in the same direction as the third extending portion. The third extending portion and the fourth extending portion are spaced apart in the radial direction, and the fourth extending portion and the third extending portion are convex relative to the third radial beam and the fourth radial beam to respectively form a third recessed portion and a fourth recessed portion on back surfaces of the fourth extending portion and the third extending portion. During assembly, the third radial beam and the fourth radial beam are respectively inserted into the first recessed portion and the second recessed portion in the radial direction, and the first extending portion and the second extending portion are respectively inserted into the third recessed portion and the fourth recessed portion and respectively at least partially overlap with and are clamped with the fourth extending portion and the third extending portion. The fourth extending portion and the third extending portion are located on one side of the clasping body, and the third radial beam and the fourth radial beam are located on the other side of the clasping body. A free end of the first extending portion faces the second connecting portion, and a free end of the third extending portion faces the first connecting portion.

Further, an energy storage arc portion on the left side arm and/or the right side arm has a width of 1.2 mm.

Further, the first clasping part includes 2, 5 or 7 teeth, and correspondingly, the second clasping part includes 1, 4 or 6 teeth; or the second clasping part includes 2, 5 or 7 teeth, and correspondingly, the first clasping part includes 1, 4 or 6 teeth.

The disclosure includes, but is not limited to, the following beneficial effects:

1) At least one clasping part is designed to be detachable from the clamp frame, and thus when removing the anastomosis clamp, the detachable clasping part can be separated from the clamp frame first and then moved away, allowing the anastomosis clamp to be removed safely and conveniently.
2) By adopting the snap-fit type detachable connection, the anastomosis clamp is convenient to detach.
3) The snap-fit type structure is disposed on different side surfaces of the clasping part, so that at the moment when the anastomosis clamp clamps the tissue after being excited, the clasping part does not shift and is connected firmly.
4) By adopting the composite fixation design combining the snap-fit type and the protruding portion-hole fitting type, when the anastomosis clamp is in use, the clasping part does not shift before and during the excitation of the anastomosis clamp, and the anastomosis clamp can be conveniently detached and removed after the wound of the patient is healed.
5) The clasping part is designed to be detachably connected to the clamp frame by means of tying. When the anastomosis clamp needs to be removed, the suture for tying can be removed to separate the clasping part can be separated from the clamp frame by untying the suture for tying, so that the anastomosis clamp can be removed conveniently.

6) By adopting the radial rotation connection structure, it can be ensured that the clasping part and the clamp frame are connected firmly, and are connected firmly in a tying state.

7) The energy storage arc portion is reinforced, so that the transient force when the anastomosis clamp is excited is increased by about 190%, and therefore, the anastomoses of the gastrointestinal wound, fistulae and bleeding points or the fixation can be better realized without affecting the subsequent detachment step.

BRIEF DESCRIPTION OF THE DRAWINGS

In order to more clearly illustrate the technical solutions in the embodiments of the disclosure, the accompanying drawings required to be used in the description of the embodiments and the prior art will be briefly described below. Apparently, the accompanying drawings in the description below are only some embodiments of the disclosure, and those of ordinary skill in the art can obtain other solutions according to these accompanying drawings without any creative work.

DETAILED DESCRIPTION OF THE EMBODIMENTS

Figure 1:
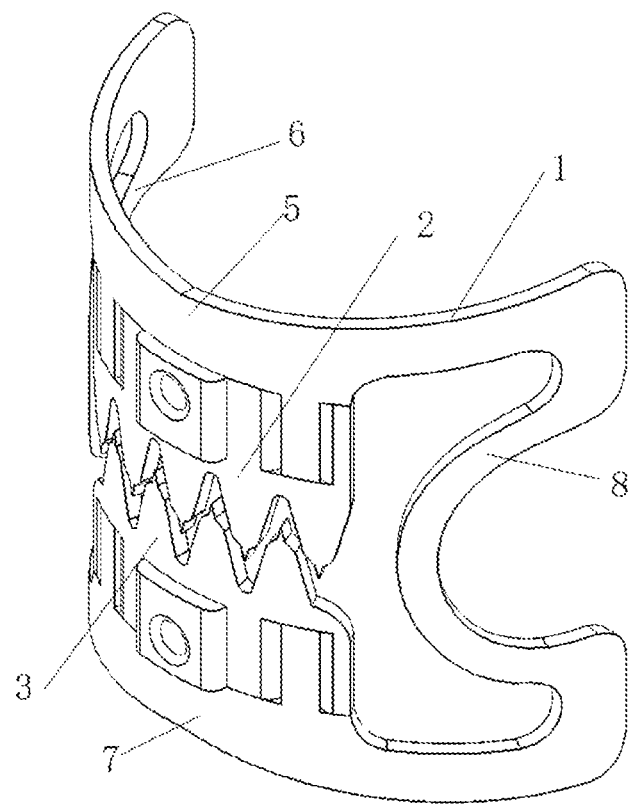
FIG. 1 is a structural schematic diagram of a first type of disassemblable anastomosis clamp according to the disclosure.
Figure 2:
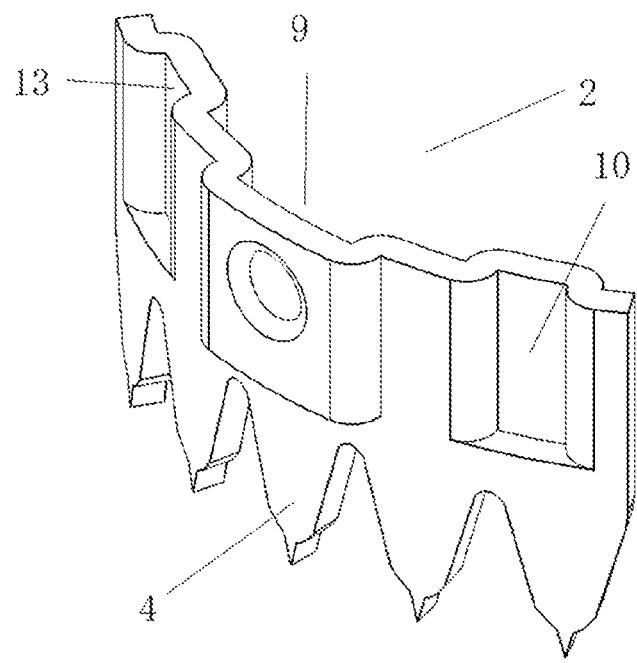
FIG. 2 is a first structural schematic diagram of a first clasping part of the first type of disassemblable anastomosis clamp according to the disclosure.
Figure 3:
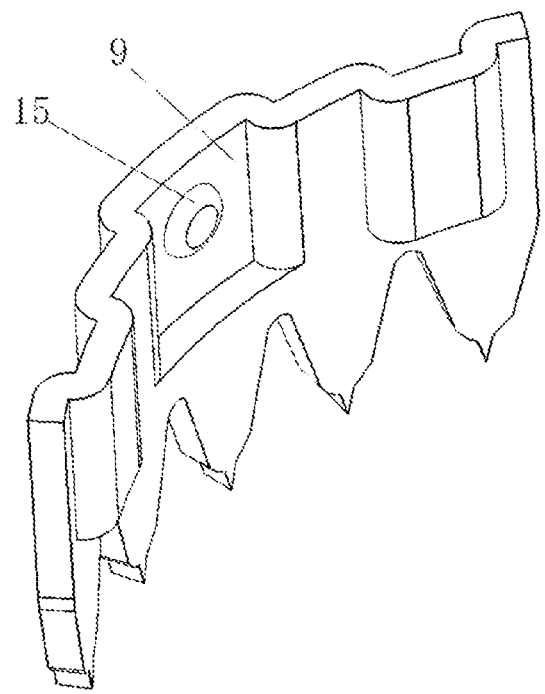
FIG. 3 is a second structural schematic diagram of the first clasping part of the first type of disassemblable anastomosis clamp according to the disclosure.
Figure 4:
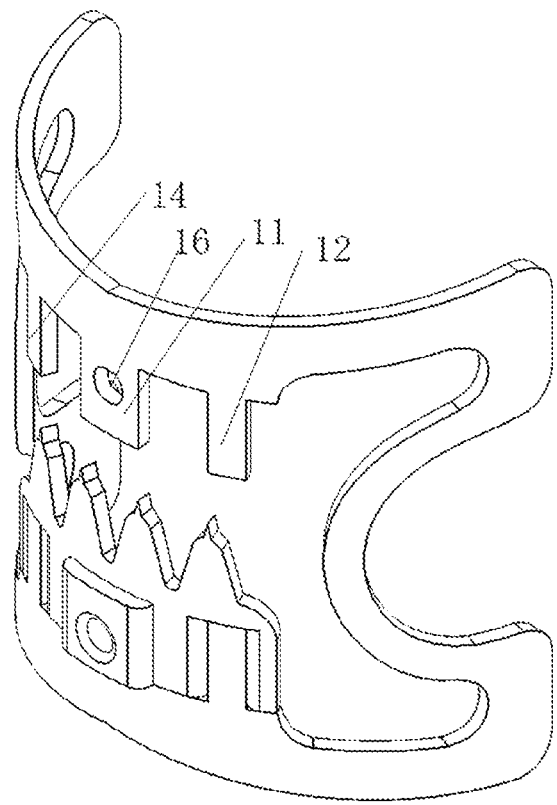
FIG. 4 is a schematic diagram of the first type of disassemblable anastomosis clamp with the first clasping part being removed according to the disclosure.
Figure 5:
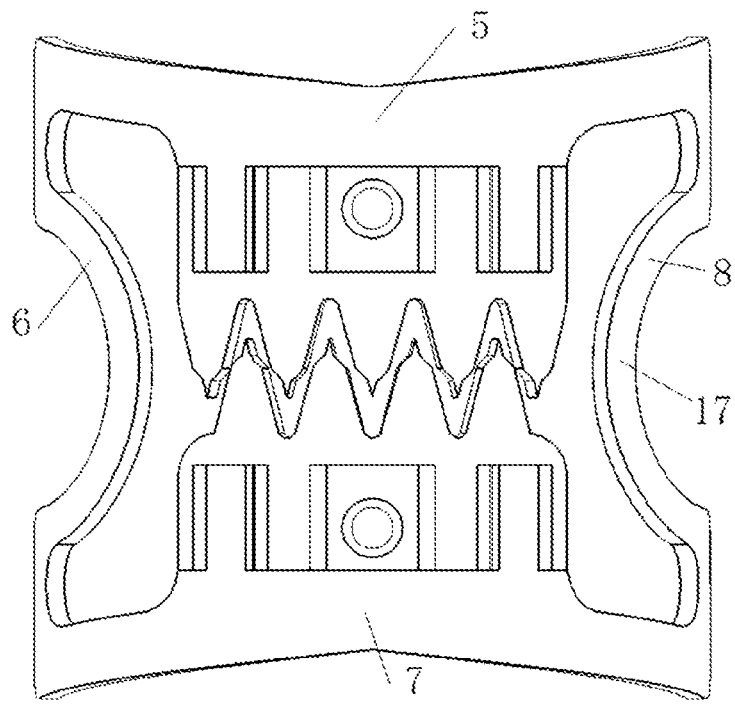
FIG. 5 is a structural front view of the first type of disassemblable anastomosis clamp according to the disclosure.
Figure 6:
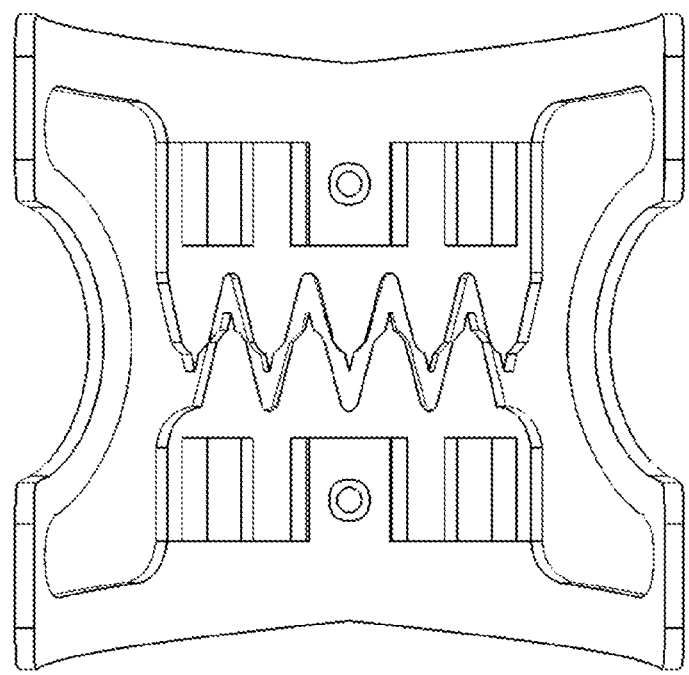
FIG. 6 is a structural rear view of the first type of disassemblable anastomosis clamp according to the disclosure.
Figure 7:
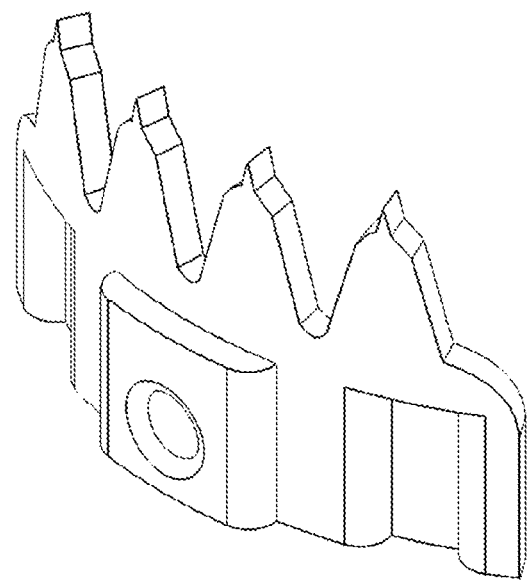
FIG. 7 is a first structural schematic diagram of a second clasping part of the first type of disassemblable anastomosis clamp according to the disclosure.
Figure 8:
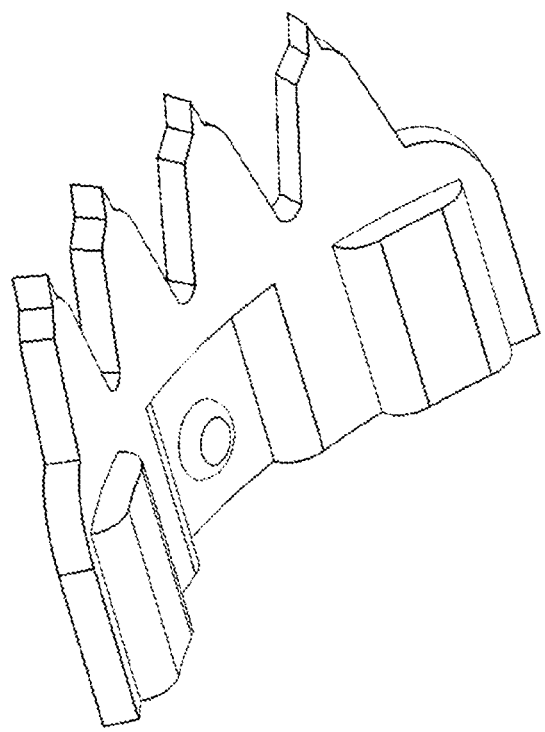
FIG. 8 is a second structural schematic diagram of the second clasping part of the first type of disassemblable anastomosis clamp according to the disclosure.
Figure 9:
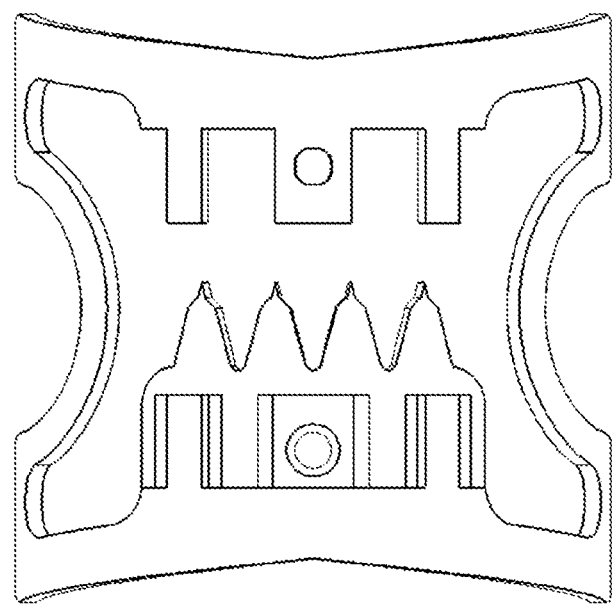
FIG. 9 is a front view of the first type of disassemblable anastomosis clamp with the first clasping part being removed according to the disclosure.
Figure 10:
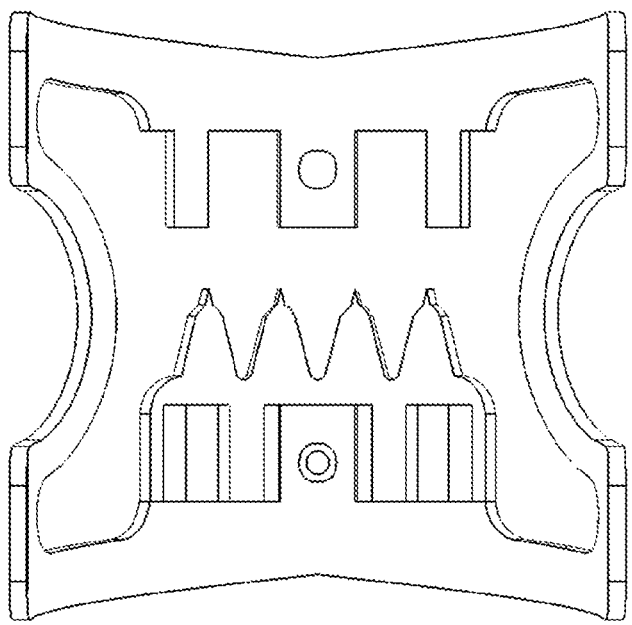
FIG. 10 is a rear view of the first type of disassemblable anastomosis clamp with the first clasping part being removed according to the disclosure.
Figure 11:
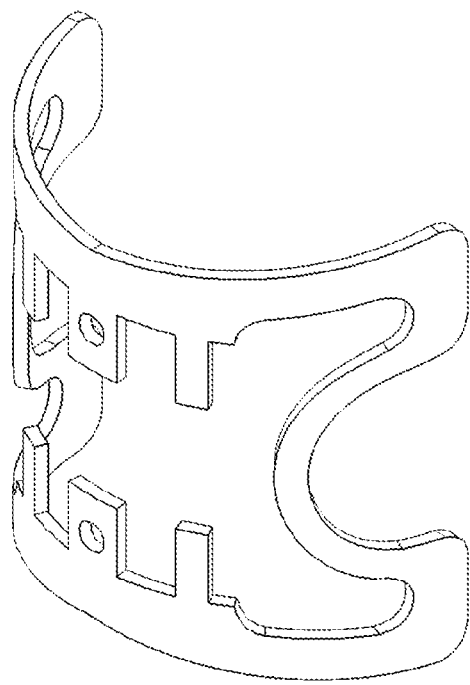
FIG. 11 is a structural schematic diagram of a clamp frame of the first type of disassemblable anastomosis clamp according to the disclosure.
Figure 12:
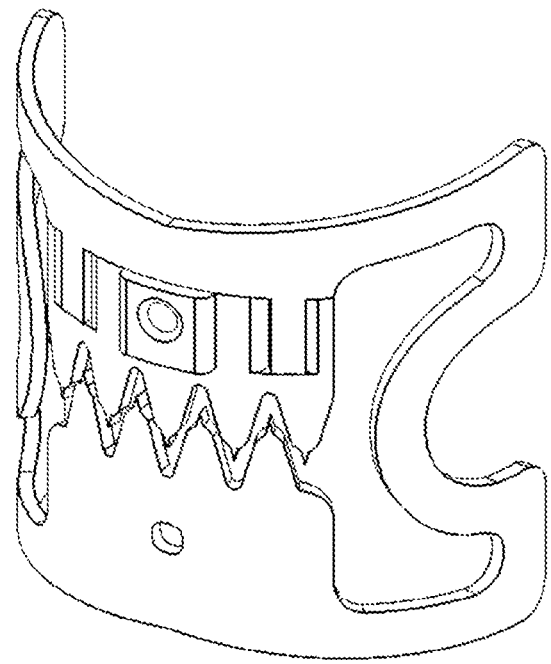
FIG. 12 is a structural schematic diagram of a second type of disassemblable anastomosis clamp according to the disclosure.
Figure 13:
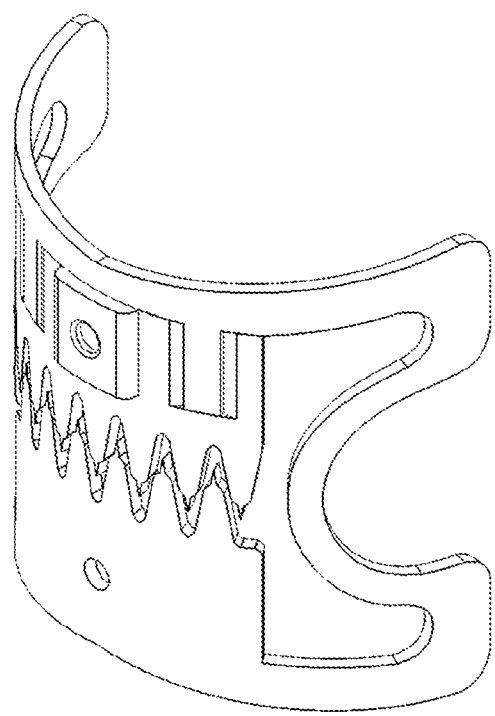
FIG. 13 is a structural schematic diagram of a third type of disassemblable anastomosis clamp according to the disclosure.
Figure 14:
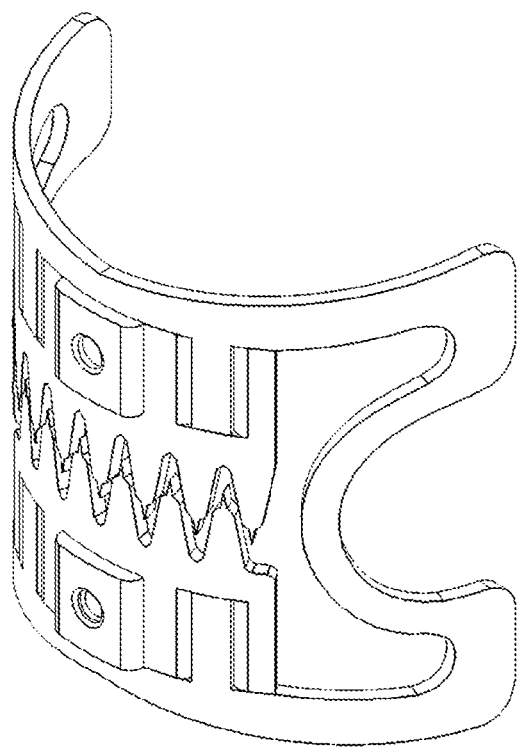
FIG. 14 is a structural schematic diagram of a fourth type of disassemblable anastomosis clamp according to the disclosure.
Figure 15:
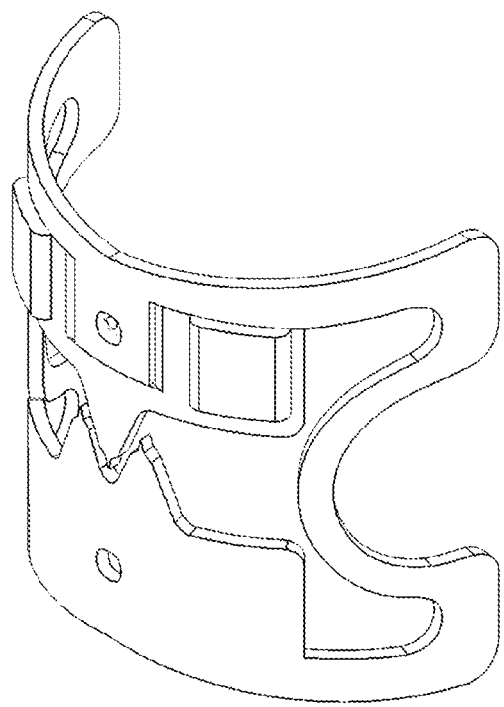
FIG. 15 is a structural schematic diagram of a fifth type of disassemblable anastomosis clamp according to the disclosure.
Figure 16:
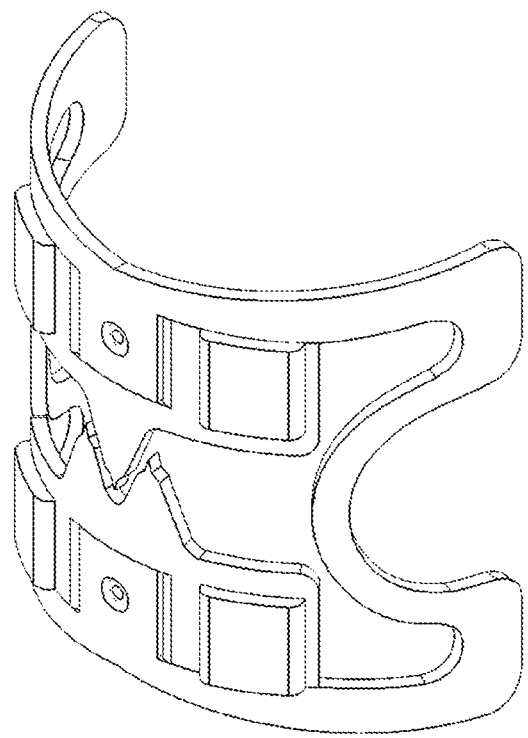
FIG. 16 is a structural schematic diagram of a sixth type of disassemblable anastomosis clamp according to the disclosure.
Figure 17:
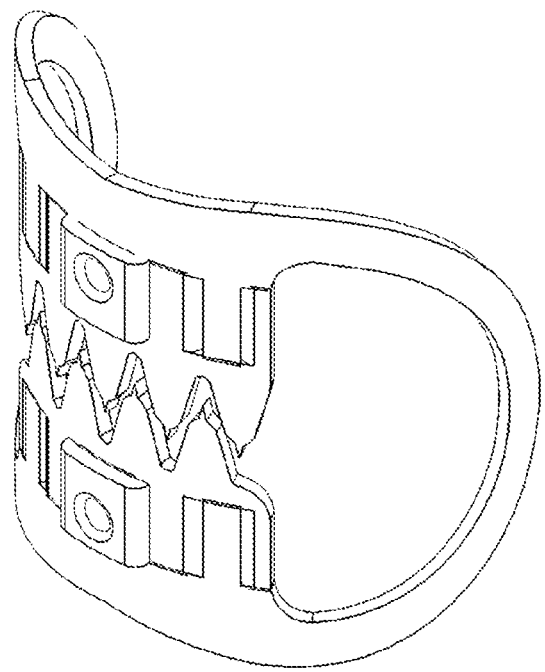
FIG. 17 is a structural schematic diagram of a seventh type of disassemblable anastomosis clamp according to the disclosure.
Figure 18:
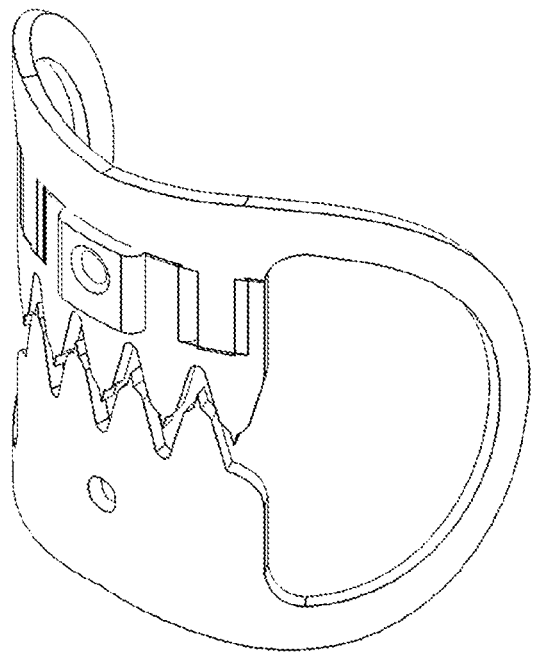
FIG. 18 is a structural schematic diagram of an eighth type of disassemblable anastomosis clamp according to the disclosure.
Figure 19:
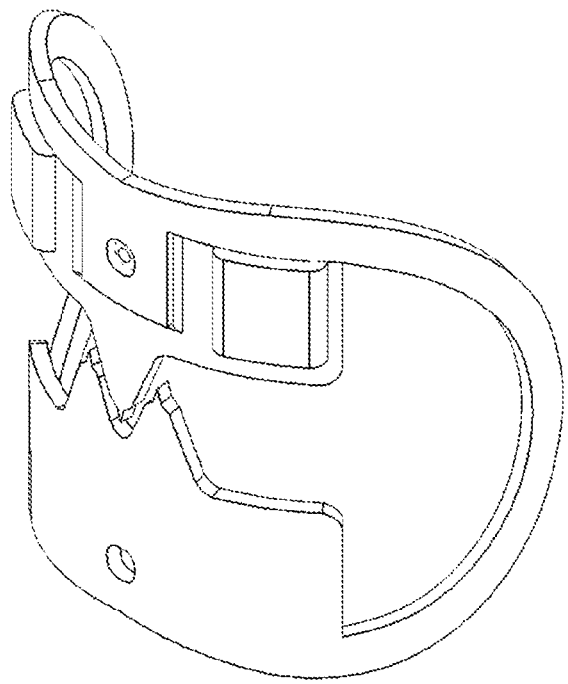
FIG. 19 is a structural schematic diagram of a ninth type of disassemblable anastomosis clamp according to the disclosure.
Figure 20:
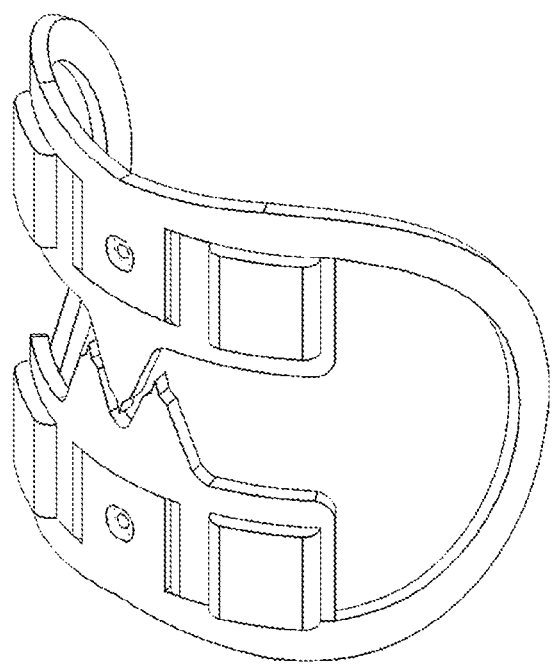
FIG. 20 is a structural schematic diagram of a tenth type of disassemblable anastomosis clamp according to the disclosure.
Figure 21:
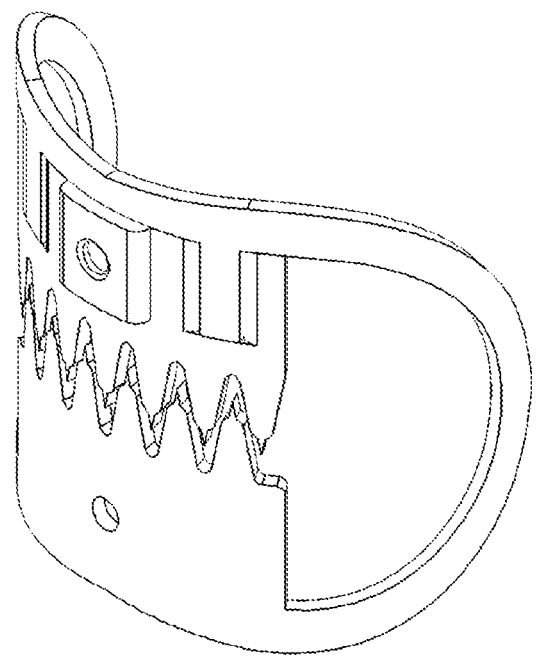
FIG. 21 is a structural schematic diagram of an eleventh type of disassemblable anastomosis clamp according to the disclosure.
Figure 22:
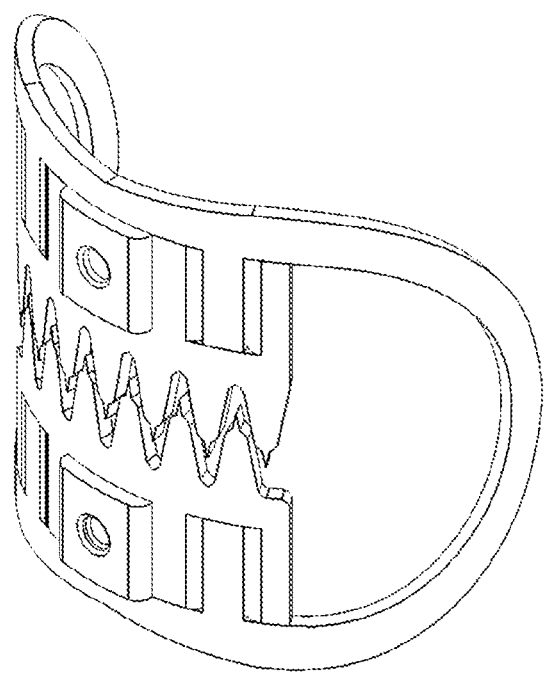
FIG. 22 is a structural schematic diagram of a twelfth type of disassemblable anastomosis clamp according to the disclosure.
Figure 23:
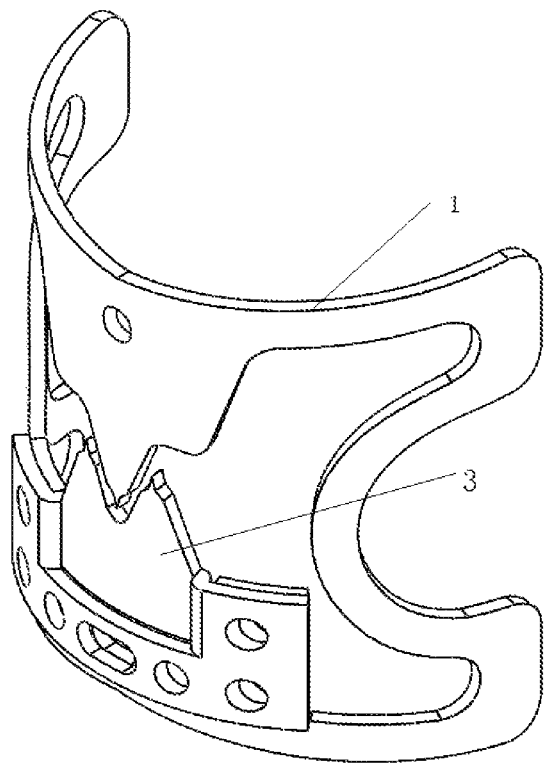
FIG. 23 is a structural schematic diagram of a thirteenth type of disassemblable anastomosis clamp according to the disclosure.
Figure 24:
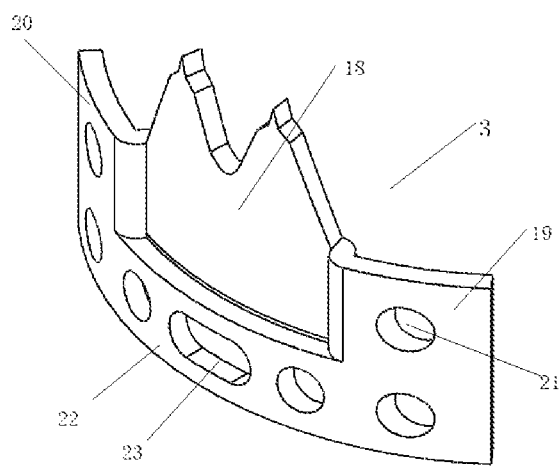
FIG. 24 is a structural schematic diagram of a second clasping part of the thirteenth type of disassemblable anastomosis clamp according to the disclosure.
Figure 25:
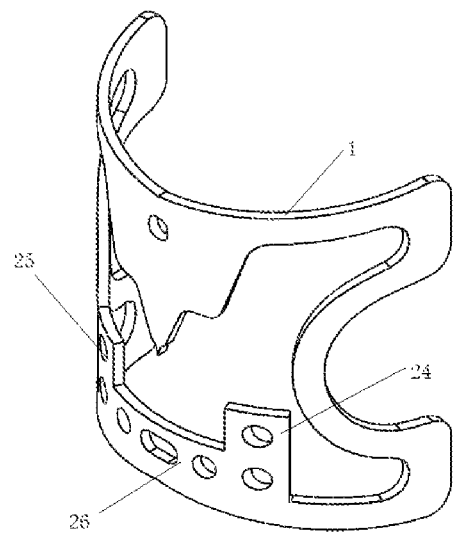
FIG. 25 is a schematic diagram of the thirteenth type of disassemblable anastomosis clamp with the second clasping part being removed according to the disclosure.
Figure 26:
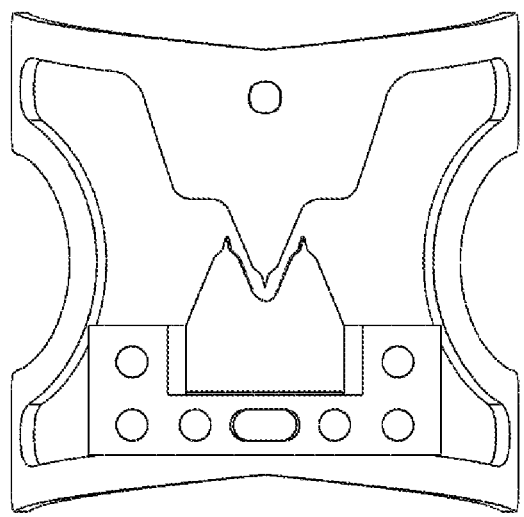
FIG. 26 is a structural front view of the thirteenth type of disassemblable anastomosis clamp according to the disclosure.
Figure 27:
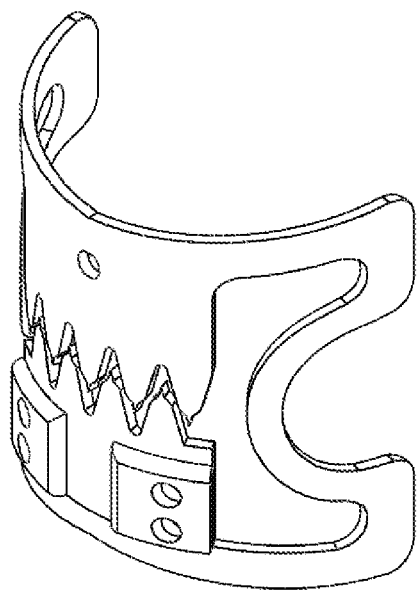
FIG. 27 is a structural schematic diagram of a fourteenth type of disassemblable anastomosis clamp according to the disclosure.
Figure 28:
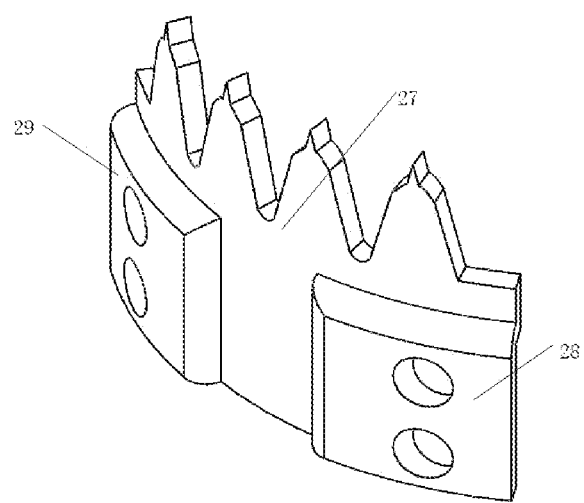
FIG. 28 is a structural schematic diagram of a second clasping part of the fourteenth type of disassemblable anastomosis clamp according to the disclosure.
Figure 29:
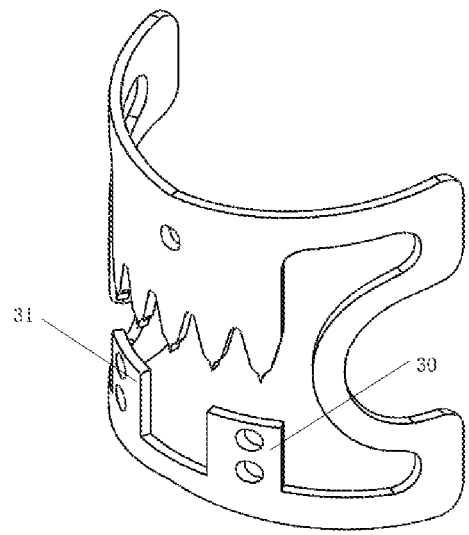
FIG. 29 is a schematic diagram of the fourteenth type of disassemblable anastomosis clamp with the second clasping part being removed according to the disclosure.
Figure 30:
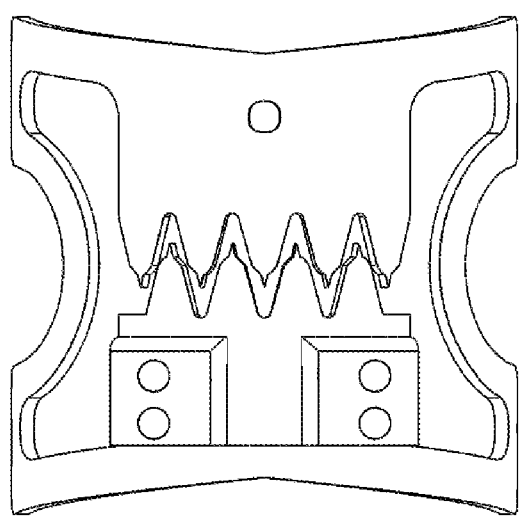
FIG. 30 is a structural front view of the fourteenth type of disassemblable anastomosis clamp according to the disclosure.
Figure 31:
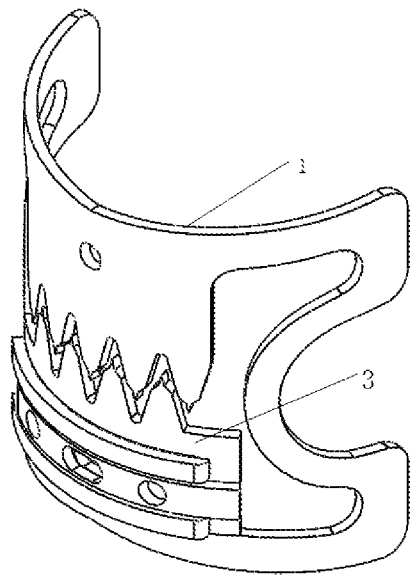
FIG. 31 is a structural schematic diagram of a fifteenth type of disassemblable anastomosis clamp according to the disclosure.
Figure 32:
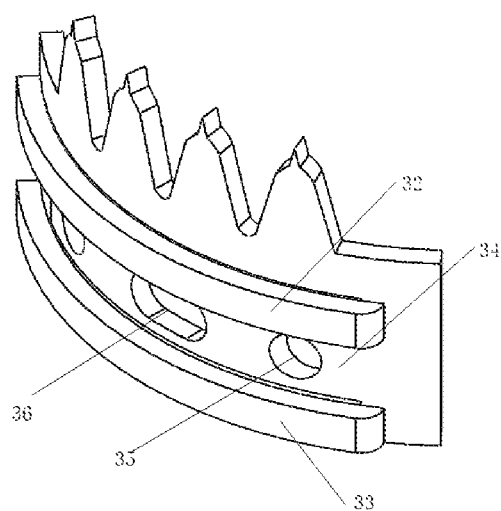
FIG. 32 is a first structural schematic diagram of a second clasping part of the fifteenth type of disassemblable anastomosis clamp according to the disclosure.
Figure 33:
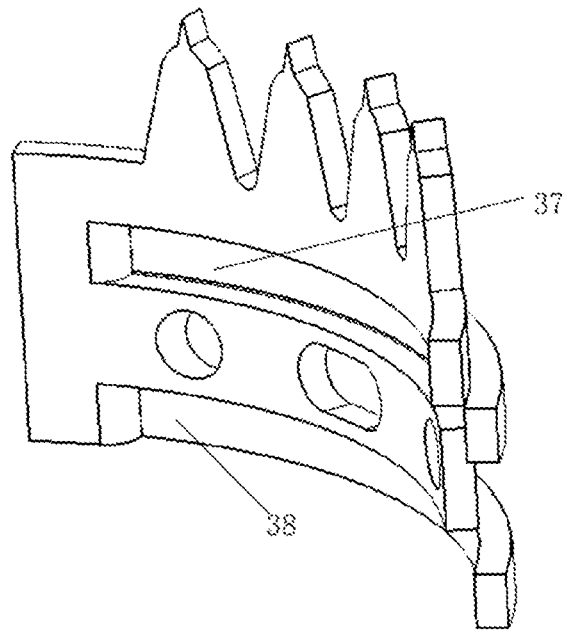
FIG. 33 is a second structural schematic diagram of the second clasping part of the fifteenth type of disassemblable anastomosis clamp according to the disclosure.
Figure 34:
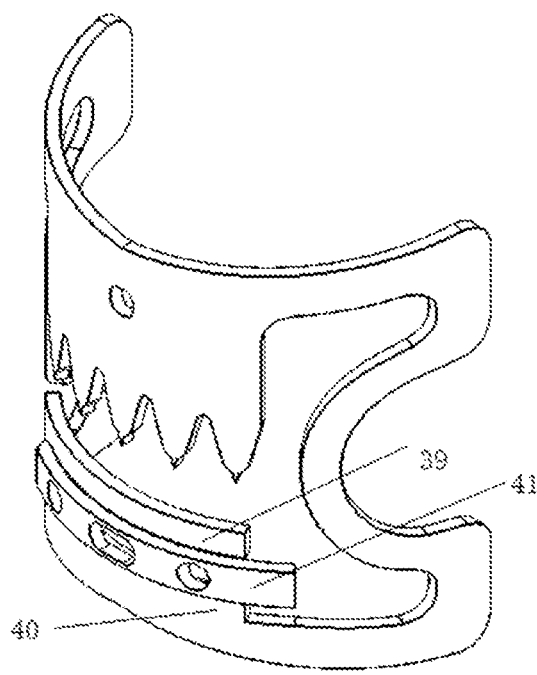
FIG. 34 is a first schematic diagram of the fifteenth type of disassemblable anastomosis clamp with the second clasping part being removed according to the disclosure.

In order to make those skilled in the art better understand the solutions of the disclosure, the technical solutions in the embodiments of the disclosure will be clearly and completely described below in conjunction with the drawings in the embodiments of the disclosure. It is apparent that the described embodiments are merely some embodiments, but not all embodiments of the disclosure. All other embodiments obtained by those of ordinary skill in the art based on the embodiments of the disclosure without creative work shall fall into the protection scope of the disclosure.

A detailed description will be given below through the specific embodiments.

As shown in FIGS. 1-12, a disassemblable anastomosis clamp includes a clamp frame 1 and a first clasping part 2 and a second clasping part 3 connected to the clamp frame 1. The first clasping part 2 and/or the second clasping part 3 is detachably connected to the clamp frame 1. At least one clasping part is designed to be detachable from the clamp frame, and thus when removing the anastomosis clamp, the detachable clasping part can be separated from the clamp frame first and then moved away, allowing the anastomosis clamp to be removed safely and conveniently. In the actual application process, those skilled in the art can choose to set all the clasping parts to be detachably connected to the clamp frame, or set one or more of the clasping parts to be detachably connected to the clamp frame. In addition, although an arc-shaped anastomosis clamp is adopted in this embodiment, those skilled in the art should understand that the detachable clasping part can also be used for anastomosis clamps in other shapes, for example, a special-shaped anastomosis clamp with 3 or more clasping parts.

In this embodiment, the clamp frame 1 is a closed outer frame. In this solution, the closed outer frame is adopted, so that it can be ensured that the disassemblable anastomosis clamp of this solution have the same outer frame structure as the existing single-piece anastomosis clamp only by designing the clasping part inside the existing single-piece anastomosis clamp to be detachable without changing the original outline structure of the single-piece anastomosis clamp, and thereby, there is no need to design the clamping cap separately. Therefore, the disassemblable anastomosis clamp of this solution has certain advantages in terms of production and design. In addition, according to the design of this solution, the existing single-piece anastomosis clamp can still be utilized after being machined/modified. It is only required to set the clasping part inside the existing single-piece anastomosis clamp to be separable and detachable.

In this embodiment, the first clasping part 2 and/or the second clasping part 3 is a toothed piece connected to the inside of the closed outer frame, and the toothed piece is provided with at least one tooth 4.

In this embodiment, the closed outer frame includes an upper arm 5, a left side arm 6, a lower arm 7 and a right side arm 8, and the upper arm 5, the left side arm 6, the lower arm 7 and the right side arm 8 are sequentially connected to form the closed outer frame.

In this embodiment, the first clasping part 2 and the second clasping part 3 are respectively connected to the upper arm 5 and the lower arm 7. The first clasping part 2 is detachably connected to the upper arm 5 and/or the second clasping part 3 is detachably connected to the lower arm 7.

In this embodiment, the first clasping part 2 and/or the second clasping part 3 includes at least one fixing groove, and the clamp frame 1 at least includes a protrusion inserted into and matched with the fixing groove. Due to the snap-fit type matching of the groove and the protrusion, the detachable connection between the clasping part and the clamp frame can be realized. Of course, those skilled in the art should understand that other detachable mechanical connections may also be used in this solution, for example, clamping connection and the like.

In this embodiment, the fixing groove includes a first fixing groove 9 and a second fixing groove 10, the first fixing groove 9 and the second fixing groove 10 are disposed on opposite side surfaces of the clasping part 2 (3), and the clamp frame 1 includes a first protrusion 11 inserted into and matched with the first fixing groove 9 and a second protrusion 12 inserted into and matched with the second fixing groove 10. By disposing the first fixing groove 9 and the second fixing groove 10 on the opposite side surfaces of the clasping part 2 (3), the two sides of the clasping part 2 (3) can be fixed respectively. For example, in this embodiment, the first fixing groove 9 is used for fixing the rear of the clasping part 2 (3), and the second fixing groove 10 is used for fixing the front of the clasping part 2 (3). In this way, it can be ensured that at the moment when the anastomosis clamp clamps the tissue after being excited, the clasping part 2 (3) does not shift.

In this embodiment, the fixing groove further includes a third fixing groove 13, the clamp frame 1 further includes a third protrusion 14 inserted into and matched with the third fixing groove 13, and the third fixing groove 13 and the first fixing groove 9 are respectively located on opposite side surfaces of the clasping part 2 (3) or the third fixing groove 13 and the second fixing groove 10 are respectively located on opposite side surfaces of the clasping part 2 (3).

In this embodiment, the second fixing groove 10 and the third fixing groove 13 are respectively located on two sides of the first fixing groove 9. The second fixing groove 10 and the third fixing groove 13 are located on a same side surface of the clasping part 2 (3). In this way, the clasping part 2 (3) can be fixed more stably, and it can be ensured that the clasping part 2 (3) does not shift in the radial direction (left-right direction).

In this embodiment, the fixing groove is formed on the clasping part 2 (3) by a lancing-type stamping process in the form of a stamped groove, and the stamping depth is the same as the thickness of the clasping part 2 (3).

In this embodiment, the first fixing groove 9 is provided with a protruding portion 15, and the first protrusion 11 is provided with a fixing hole 16 matched with the protruding portion 15. The protruding portion 15 is clamped with the fixing hole 16, so that the clasping part 2 (3) will not shift in the axial direction (up-down direction) after the clasping part 2 (3) and the clamp frame 1 are assembled. Preferably, the protruding portion 15 is perpendicular to the bottom surface of the first fixing groove 9. Of course, those skilled in the art should understand that the protruding portion 15 may also be disposed on the first protrusion 11, and correspondingly, the fixing hole 16 is disposed in the first fixing groove 9. In addition, the protruding portion or the fixing hole may be disposed on the second fixing groove 10, and correspondingly, the fixing hole or the protruding portion may be disposed on the second protrusion 12; or the protruding portion or the fixing hole may be disposed on the third fixing groove 13, and correspondingly, the fixing hole or the protruding portion may be disposed on the third protrusion 14. Preferably, all the fixing grooves may be provided with the protruding portions or the fixing holes, and correspondingly, all the protrusions may be provided with the fixing holes or the protruding portions. In this solution, by adopting the composite fixation design combining the snap-fit type and the protruding portion-hole fitting type, when the anastomosis clamp is in use, the clasping part does not shift before and during the excitation of the anastomosis clamp, and the anastomosis clamp can be conveniently detached and removed after the wound of the patient is healed.

In this embodiment, the protruding portion 15 is a hemispherical protrusion, and specifically, may be formed by downward stamping by a deep drawing process.

As shown in FIGS. 23-26, the disclosure provides another disassemblable anastomosis clamp, which is different from the anastomosis clamp shown in FIGS. 1-12 in that: the second clasping part 3 in this embodiment is detachably connected to the clamp frame 1 through a (medical) suture. Of course, the first clasping part 2 may also be detachably connected to the clamp frame 1 in the same manner as the second clasping part 3.

In this embodiment, the second clasping part 3 includes a clasping body 18 and a tying body fixedly connected to the clasping body 18, and the tying body includes at least one tying hole. The clamp frame 1 includes a tying body cooperation portion cooperating with the tying body, and the tying body cooperation portion includes at least one hole cooperating with the tying hole in the tying body. Of course, the tying hole may also be located in any position of the clasping body, and correspondingly, the tying hole in the clamp frame may also be located in any position of the clamp frame, as long as the clasping part and the clamp frame can be tied.

In this embodiment, the tying body includes a first tying body 19 and a second tying body 20 that are symmetrically fixed to two sides of the clasping body 18, and the first tying body 19 and the second tying body 20 each include at least one tying hole 21. Correspondingly, the tying body cooperation portion includes a first cooperation portion 24 cooperating with the first tying body 19 and a second cooperation portion 25 cooperating with the second tying body 20, and the first cooperation portion 24 and the second cooperation portion 25 include holes cooperating with the tying holes in the first tying body 19 and the second tying body 20.

In this embodiment, the anastomosis clamp further includes a third tying body 22 fixedly connected to the first tying body 19, the second tying body 20 and the clasping body 18 and located therebelow. The third tying body 22 includes at least one tying hole, and one of the tying holes 23 is a slotted hole located in the middle of the third tying body 22. Correspondingly, the tying body cooperation portion includes a third cooperation portion 26 cooperating with the third tying body 22, and the third cooperation portion 26 includes at least one hole cooperating with the tying hole in the third tying body 22, and a slotted hole cooperating with a slotted hole in the third tying body 22.

In this embodiment, the first tying body 19, the second tying body 20, the clasping body 18 and the third tying body 22 are integrally formed.

As shown in FIGS. 27-30, the disclosure provides still another disassemblable anastomosis clamp, of which the principle is similar to that of the anastomosis clamp shown in FIGS. 23-26. The second clasping part 3 is also detachably connected to the clamp frame 1 through a (medical) suture. The difference is that: the disassemblable anastomosis clamp in this embodiment does not include the third tying body 22. Specifically, the second clasping part 3 includes a clasping body 27 and a tying body fixedly connected to the clasping body 27, and the tying body includes at least one tying hole. The clamp frame 1 includes a tying body cooperation portion cooperating with the tying body, and the tying body cooperation portion includes at least one hole cooperating with the tying hole in the tying body. Of course, the tying hole may also be located in any position of the clasping body, and correspondingly, the tying hole in the clamp frame may also be located in any position of the clamp frame, as long as the clasping part and the clamp frame can be tied. Of course, the first clasping part 2 may also be detachably connected to the clamp frame 1 in the same manner as the second clasping part 3.

In this embodiment, the tying body includes a first tying body 28 and a second tying body 29 that are symmetrically fixed to two sides of the clasping body 27, and the first tying body 28 and the second tying body 29 each include at least one tying hole. Correspondingly, the tying body cooperation portion includes a first cooperation portion 30 cooperating with the first tying body 28 and a second cooperation portion 31 cooperating with the second tying body 29, and the first cooperation portion 30 and the second cooperation portion 31 include holes cooperating with the tying holes in the first tying body 28 and the second tying body 29.

As shown in FIGS. 31-37, the disclosure provides yet another disassemblable anastomosis clamp, of which the principle is similar to that of the anastomosis clamp shown in FIGS. 23-30. The second clasping part 3 is also detachably connected to the clamp frame 1 through a (medical) suture. The difference is that: the second clasping part 3 is matched with the clamp frame 1 through a radial rotation structure.

Figure 35:
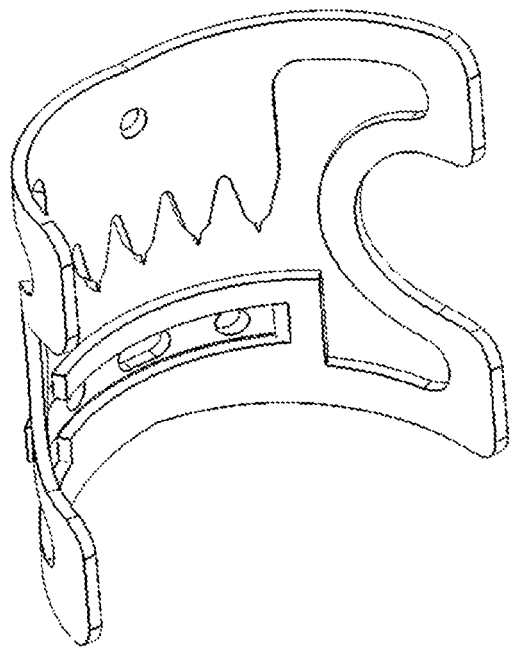
FIG. 35 is a second schematic diagram of the fifteenth type of disassemblable anastomosis clamp with the second clasping part being removed according to the disclosure.
Figure 36:
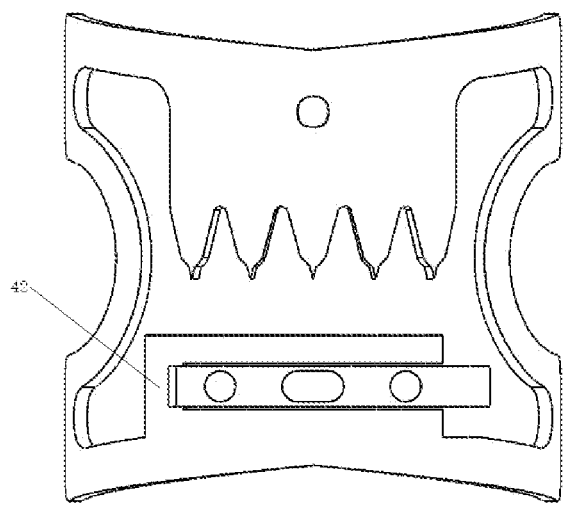
FIG. 36 is a front view of the fifteenth type of disassemblable anastomosis clamp with the second clasping part being removed according to the disclosure.
Figure 37:
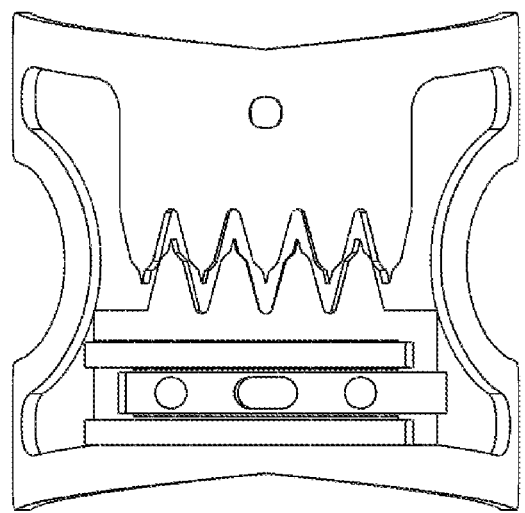
FIG. 37 is a structural front view of the fifteenth type of disassemblable anastomosis clamp according to the disclosure.
Figure 38:
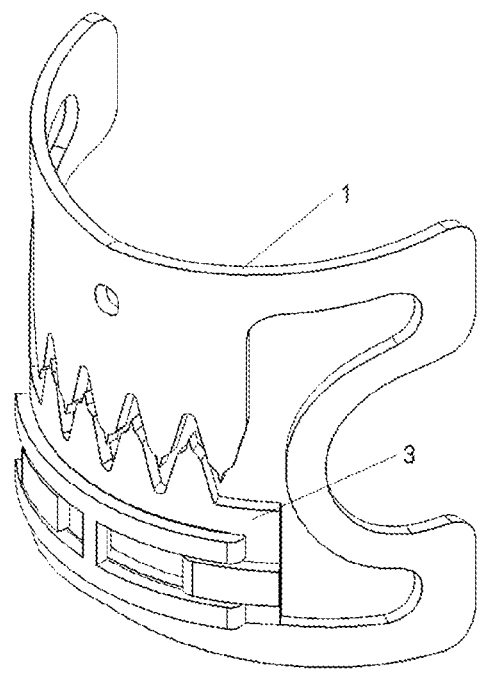
FIG. 38 is a first structural schematic diagram of a sixteenth type of disassemblable anastomosis clamp according to the disclosure.

In this embodiment, the second clasping part 3 includes a clasping body, the clasping body includes a first radial beam 32 and a second radial beam 34, a back surface of the first radial beam 32 is concave relative to the second radial beam 34 to form a first recessed portion 37, and the second radial beam 34 includes at least one tying hole 35. Correspondingly, the clamp frame 1 includes a third radial beam 39 matched with the first radial beam 32 and a fourth radial beam 41 matched with the second radial beam 34, a back surface of the fourth radial beam 41 is concave relative to the third radial beam 39 to form a second recessed portion (as shown in FIG. 35), and the fourth radial beam 41 includes at least one hole cooperating with the tying hole in the second radial beam 34. The third radial beam 39 is inserted into the first recessed portion 37, and the second radial beam 34 is inserted into the second recessed portion. Of course, the tying hole may also be located in any position of the first radial beam or the clasping body, and correspondingly, the tying hole in the clamp frame may also be located in any position of the third radial beam or the clamp frame, as long as the clasping part and the clamp frame can be tied.

In this embodiment, a front surface of the fourth radial beam 41 is convex relative to the third radial beam 39, and a front surface of the first radial beam 32 is convex relative to the second radial beam 34.

In this embodiment, the second radial beam 34 further includes a slotted hole 36 located in the middle, and correspondingly, the fourth radial beam includes a slotted hole cooperating with a slotted hole in the second radial beam 34.

In this embodiment, the anastomosis clamp further includes a fifth radial beam 33. The fifth radial beam 33 and the first radial beam 32 are symmetrically disposed on two sides of the second radial beam 34. Correspondingly, the clamp frame 1 includes a sixth radial beam 40 matched with the fifth radial beam 33.

In this embodiment, a back surface of the fifth radial beam 33 is concave relative to the second radial beam 34 to form a third recessed portion 38. The sixth radial beam 40 is inserted into the third recessed portion 38.

In this embodiment, by combining the radial rotation matching with the concave-convex matching of the beams, the clasping part can be stably fixed to the clamp frame, thereby forming the stable anastomosis clamp.

In this embodiment, the third radial beam 39, the sixth radial beam 40 and the fourth radial beam 41 are integrally connected by a vertical portion 42.

In this embodiment, the second clasping part 3 (or the second clasping part 2) and the clamp frame 1 are each an integrally formed structure.

As shown in FIGS. 38-45, the disclosure provides yet still another disassemblable anastomosis clamp, of which the principle is similar to that of the anastomosis clamp shown in FIGS. 31-37. The second clasping part 3 is matched with the clamp frame 1 also in a radial rotation manner, but through a different radial rotation structure.

Figure 39:
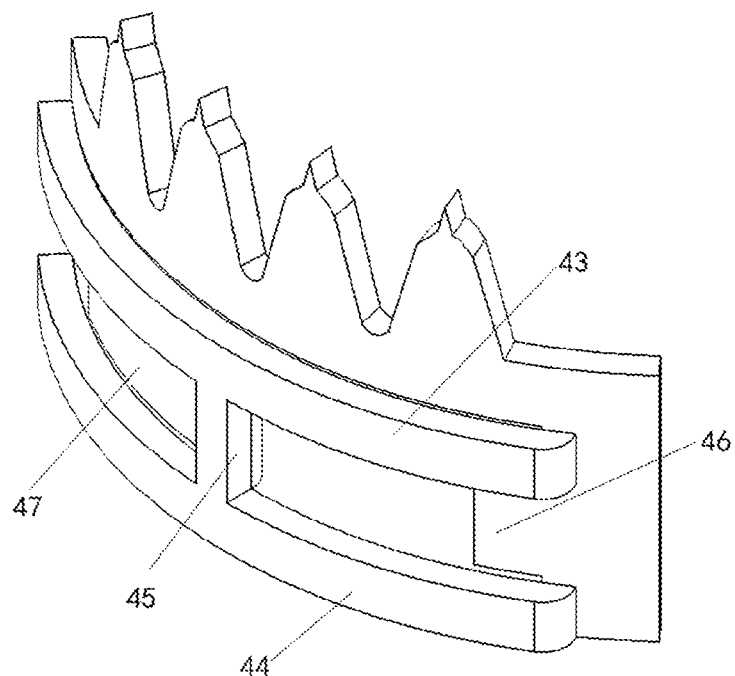
FIG. 39 is a first structural schematic diagram of a second clasping part of the sixteenth type of disassemblable anastomosis clamp according to the disclosure.
Figure 40:
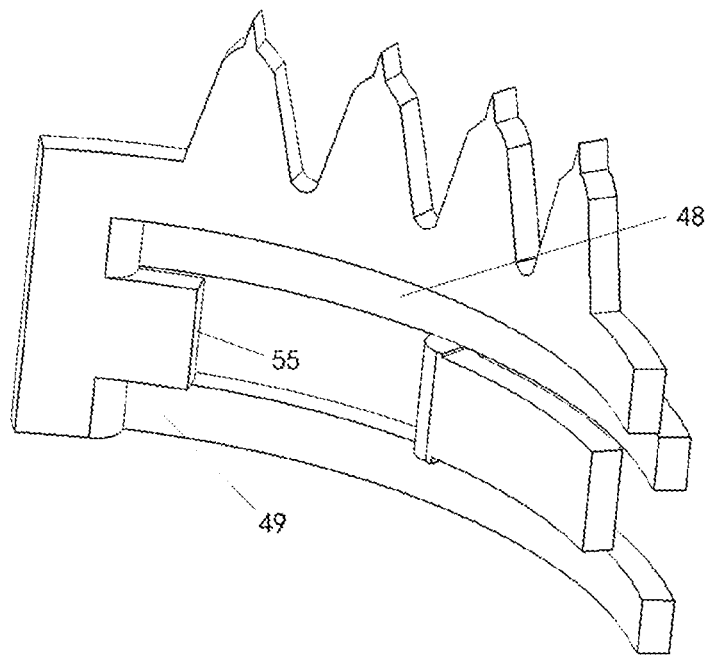
FIG. 40 is a second structural schematic diagram of the second clasping part of the sixteenth type of disassemblable anastomosis clamp according to the disclosure.
Figure 41:
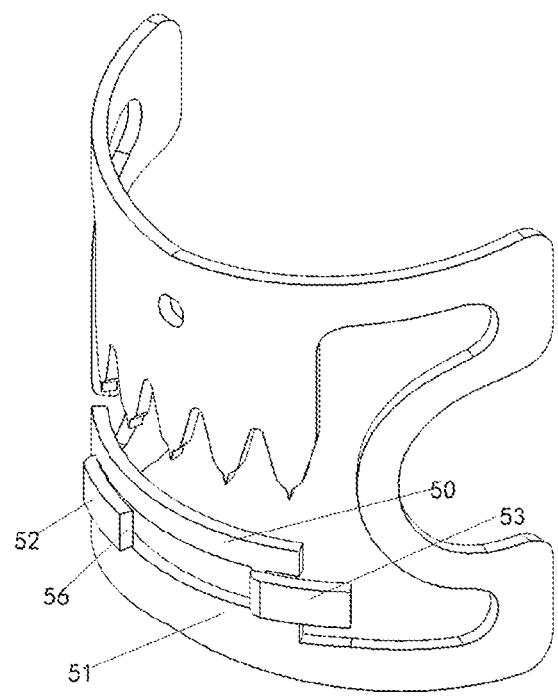
FIG. 41 is a first schematic diagram of the sixteenth type of disassemblable anastomosis clamp with the second clasping part being removed according to the disclosure.
Figure 42:
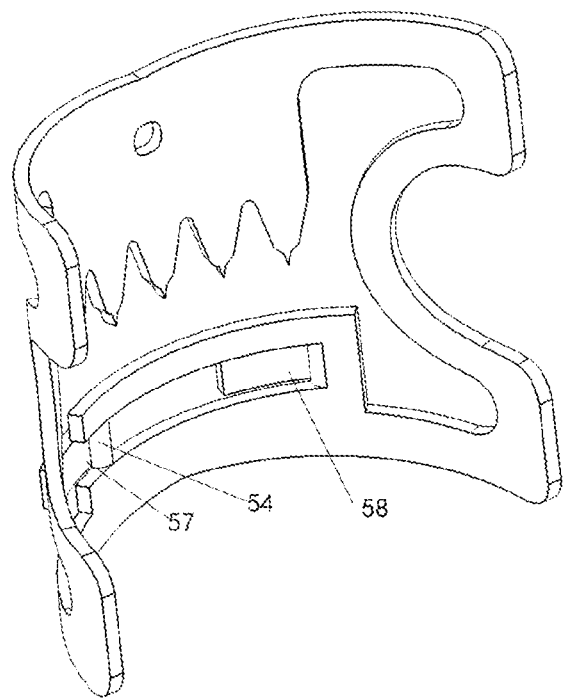
FIG. 42 is a second schematic diagram of the sixteenth type of disassemblable anastomosis clamp with the second clasping part being removed according to the disclosure.
Figure 43:
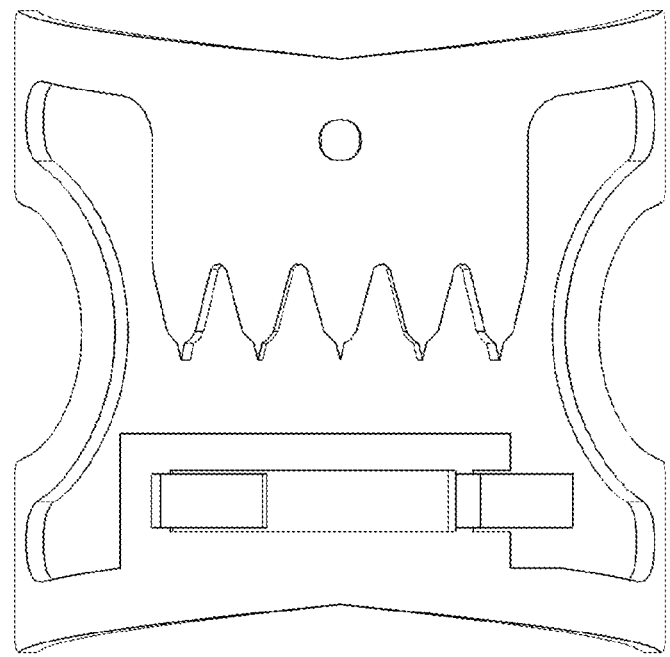
FIG. 43 is a front view of the sixteenth type of disassemblable anastomosis clamp with the second clasping part being removed according to the disclosure.
Figure 44:
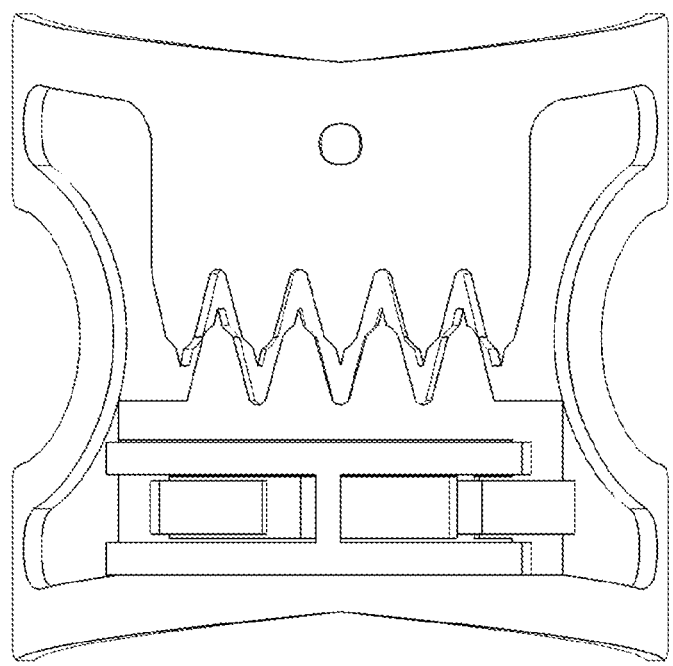
FIG. 44 is a structural front view of the sixteenth type of disassemblable anastomosis clamp according to the disclosure.
Figure 45:
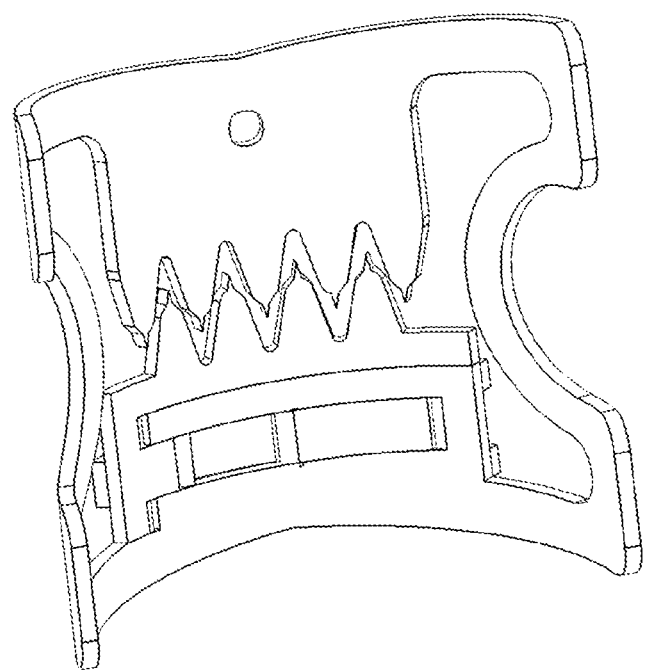
FIG. 45 is a second structural schematic diagram of the sixteenth type of disassemblable anastomosis clamp according to the disclosure.

In this embodiment, the second clasping part 3 includes a clasping body, and the clasping body includes a first radial beam 43, a second radial beam 44 and a first extending portion 46 located between the first radial beam 43 and the second radial beam 44 and extending at a same position in a same radial direction as the first radial beam 43 and the second radial beam 44. A first connecting portion 45 is also provided between the first radial beam 43 and the second radial beam 44, and the first connecting portion 45 is connected with a second extending portion 47 extending in the same direction as the first extending portion 46. The first extending portion 46 and the second extending portion 47 are spaced apart in the radial direction (i.e., have a spacing therebetween, as shown in FIGS. 39-40), and the first radial beam 43 and the second radial beam 44 are convex relative to the first extending portion 46 and the second extending portion 47 to respectively form a first recessed portion 48 and a second recessed portion 49 on back surfaces of the first radial beam 43 and the second radial beam 44. Correspondingly, the clamp frame 1 includes a third radial beam 50 matched with the first radial beam 43 and a fourth radial beam 51 matched with the second radial beam 44, and a third extending portion 52 located between the third radial beam 50 and the fourth radial beam 51 and extending at a same position in a same radial direction as the third radial beam 50 and the fourth radial beam 51. A second connecting portion 54 is also provided between the third radial beam 50 and the fourth radial beam 51, and the second connecting portion 54 is connected with a fourth extending portion 53 extending in the same direction as the third extending portion 52. The third extending portion 52 and the fourth extending portion 53 are spaced apart in the radial direction (i.e., have a spacing therebetween, as shown in FIGS. 41-42), and the fourth extending portion 53 and the third extending portion 52 are convex relative to the third radial beam 50 and the fourth radial beam 51 to respectively form a third recessed portion 57 and a fourth recessed portion 58 on back surfaces of the fourth extending portion 53 and the third extending portion 52 (as shown in FIG. 42). During assembly, the third radial beam 50 and the fourth radial beam 51 are respectively inserted into the first recessed portion 48 and the second recessed portion 49 in the radial direction, and the first extending portion 46 and the second extending portion 47 are respectively inserted into the third recessed portion 57 and the fourth recessed portion 58 and respectively at least partially overlap with and are clamped with the fourth extending portion 53 and the third extending portion 52. The fourth extending portion 53 and the third extending portion 52 are located on one side of the clasping body, and the third radial beam 50 and the fourth radial beam 51 are located on the other side of the clasping body. A free end 55 of the first extending portion 46 faces the second connecting portion 54, and a free end 56 of the third extending portion 52 faces the first connecting portion 45.

In this embodiment, through the radial rotation matching, the concave-convex staggered matching of the beams and the staggered clamping of the first extending portion and the second extending portion with the fourth extending portion and the third extending portion, the clasping part is fixed to the clamp frame, thereby forming the stable anastomosis clamp without tying.

In this embodiment, the clamp frame and the second clasping part are each an integrally formed structure.

Preferably, the left side arm 6 and the right side arm 8 are of an inward arc structure or an outward arc structure to respectively form an inward arc clamp (as shown in FIGS. 1, 12-16 and 23-36) or an outward arc clamp (as shown in FIGS. 17-22). Compared with the inward arc clamp, the outward arc clamp can clip a larger wound surface, and produces less friction on the tissue and thus lower risk of injury due to its outward arc structure.

Preferably, an energy storage arc portion 17 on the left side arm 6 and/or the right side arm 8 has a width of 1.2 mm By increasing the width from existing 1 mm to 1.2 mm, the energy storage arc portion is reinforced, so that the transient force when the anastomosis clamp is excited is increased by about 190%, and therefore, the anastomoses of the gastrointestinal wound, fistulae and bleeding points or the fixation can be better realized without affecting the subsequent detachment step.

Preferably, the first clasping part 2 and the second clasping part 3 are both detachably connected to the clamp frame 1. As mentioned above, the first clasping part 2 and the second clasping part 3 are detachably connected to the clamp frame 1 preferably in the same manner.

Preferably, the first clasping part 2 includes 2, 5 or 7 teeth, and correspondingly, the second clasping part 3 includes 1, 4 or 6 teeth, so that a 3-tooth, 9-tooth or 13-tooth anastomosis clamp is formed. Of course, those skilled in the art should understand that the second clasping part 3 may include 2, 5 or 7 teeth, and correspondingly, the first clasping part 2 may include 1, 4 or 6 teeth, as shown in FIGS. 1-36.

Preferably, the disassemblable anastomosis clamp is made of titanium-based shape-memory alloy, or the clasping part is made of medical stainless steel material and the clamp frame is made of titanium-based shape-memory alloy.

The foregoing is a further detailed description of the disclosure in conjunction with the specific preferred embodiments. The specific implementation of the disclosure should not be construed as limited to this description. A person of ordinary skill in the technical field to which the disclosure belongs can also make some simple deductions or substitutions without departing from the concept of the disclosure, all of which should be regarded as falling within the protection scope of the disclosure.

INDUSTRIAL APPLICABILITY

According to the anastomosis clamp provided by the disclosure, at least one clasping part is designed to be detachable from the clamp frame, and thus when removing the anastomosis clamp, the detachable clasping part can be separated from the clamp frame first and then moved away, allowing the anastomosis clamp to be removed safely and conveniently. Therefore, the anastomosis clamp provided by the disclosure has industrial applicability.

What is claimed is:

1. A disassemblable anastomosis clamp, at least comprising a clamp frame and a first clasping part and a second clasping part connected to the clamp frame, wherein the first clasping part and/or the second clasping part is detachably connected to the clamp frame, wherein the first clasping part and/or the second clasping part is detachably connected to the clamp frame by means of tying, wherein the first clasping part and/or the second clasping part comprises a clasping body, the clasping body comprises a first radial beam and a second radial beam, and a back surface of the first radial beam is concave relative to the second radial beam to form a first recessed portion; correspondingly, the clamp frame comprises a third radial beam matched with the first radial beam and a fourth radial beam matched with the second radial beam, and a back surface of the fourth radial beam is concave relative to the third radial beam to form a second recessed portion; the third radial beam is inserted into the first recessed portion, and the second radial beam is inserted into the second recessed portion; and the second radial beam and/or the first radial beam comprises at least one tying hole, and the fourth radial beam and/or the third radial beam comprises at least one hole cooperating with the tying hole.

2. The anastomosis clamp according to claim 1, further comprising a fifth radial beam, wherein the fifth radial beam and the first radial beam are symmetrically disposed on two sides of the second radial beam; correspondingly, the clamp frame comprises a sixth radial beam matched with the fifth radial beam.

3. A disassemblable anastomosis clamp, at least comprising a clamp frame and a first clasping part and a second clasping part connected to the clamp frame, wherein the first clasping part and/or the second clasping part is detachably connected to the clamp frame, wherein the first clasping part and/or the second clasping part comprises a clasping body, the clasping body comprises a first radial beam, a second radial beam and a first extending portion located between the first radial beam and the second radial beam and extending at a same position in a same radial direction as the first radial beam and the second radial beam, a first connecting portion is also provided between the first radial beam and the second radial beam, and the first connecting portion is connected with a second extending portion extending in the same direction as the first extending portion, wherein the first extending portion and the second extending portion are spaced apart in the radial direction, and the first radial beam and the second radial beam are convex relative to the first extending portion and the second extending portion to respectively form a first recessed portion and a second recessed portion on back surfaces of the first radial beam and the second radial beam; correspondingly, the clamp frame comprises a third radial beam matched with the first radial beam and a fourth radial beam matched with the second radial beam, and a third extending portion located between the third radial beam and the fourth radial beam and extending at a same position in a same radial direction as the third radial beam and the fourth radial beam, a second connecting portion is also provided between the third radial beam and the fourth radial beam, and the second connecting portion is connected with a fourth extending portion extending in the same direction as the third extending portion, wherein the third extending portion and the fourth extending portion are spaced apart in the radial direction, and the fourth extending portion and the third extending portion are convex relative to the third radial beam and the fourth radial beam to respectively form a third recessed portion and a fourth recessed portion on back surfaces of the fourth extending portion and the third extending portion; and during assembly, the third radial beam and the fourth radial beam are respectively inserted into the first recessed portion and the second recessed portion in the radial direction, the first extending portion and the second extending portion are respectively inserted into the third recessed portion and the fourth recessed portion and respectively at least partially overlap with and are clamped with the fourth extending portion and the third extending portion, the fourth extending portion and the third extending portion are located on one side of the clasping body, the third radial beam and the fourth radial beam are located on the other side of the clasping body, a free end of the first extending portion faces the second connecting portion, and a free end of the third extending portion faces the first connecting portion.

* * * * *